United States Patent [19]

Nevin

[11] Patent Number: 5,580,245
[45] Date of Patent: Dec. 3, 1996

[54] AMALGAM CARRIER

[76] Inventor: Donald M. Nevin, 3 Clearmeadow Ct., Woodbury, N.Y. 11791

[21] Appl. No.: 382,685

[22] Filed: Feb. 2, 1995

[51] Int. Cl.$^6$ ..................................................... A61C 5/04
[52] U.S. Cl. .................................................................. 433/90
[58] Field of Search .................................... 433/90, 89, 80

[56] References Cited

U.S. PATENT DOCUMENTS

| | | | |
|---|---|---|---|
| 2,476,793 | 7/1949 | Arena | 433/90 |
| 2,679,102 | 5/1954 | Ivory, Jr. | 433/90 |
| 3,735,492 | 5/1973 | Karter et al. | 433/90 |
| 4,273,534 | 6/1981 | Seid | 433/90 |
| 4,515,563 | 5/1985 | Dungill | 433/90 |
| 4,673,353 | 6/1987 | Nevin | 433/90 |
| 4,767,325 | 8/1988 | Kopunek et al. | 433/90 |

*Primary Examiner*—Paul J. Hirsch
*Attorney, Agent, or Firm*—James & Franklin; Robert L. Epstein, Esq.; Harold James, Esq.

[57] ABSTRACT

The functional portion of the instrument includes a pin and lever assembly. One end of the pin is received in an opening in the handle. The other end of the pin is bent into a "U" shape to form a plunger. The lever, which carries a cylinder, is mounted on and moveable relative to the pin. As the lever is moved relative to the pin, the plunger moves within the cylinder to dispense the amalgam. The lever is held on the pin by a bias spring which extends from the handle. A flexible element within the handle normally engages the pin end to retain the assembly on the handle. Depression of a button on the exterior of the handle causes the internal element to flex to disengage the pin end. The assembly may then be easily removed from the handle as a unit by disengaging the bias spring from the lever. This facilitates thorough cleaning of all parts of the instrument and reassembly thereof.

15 Claims, 4 Drawing Sheets

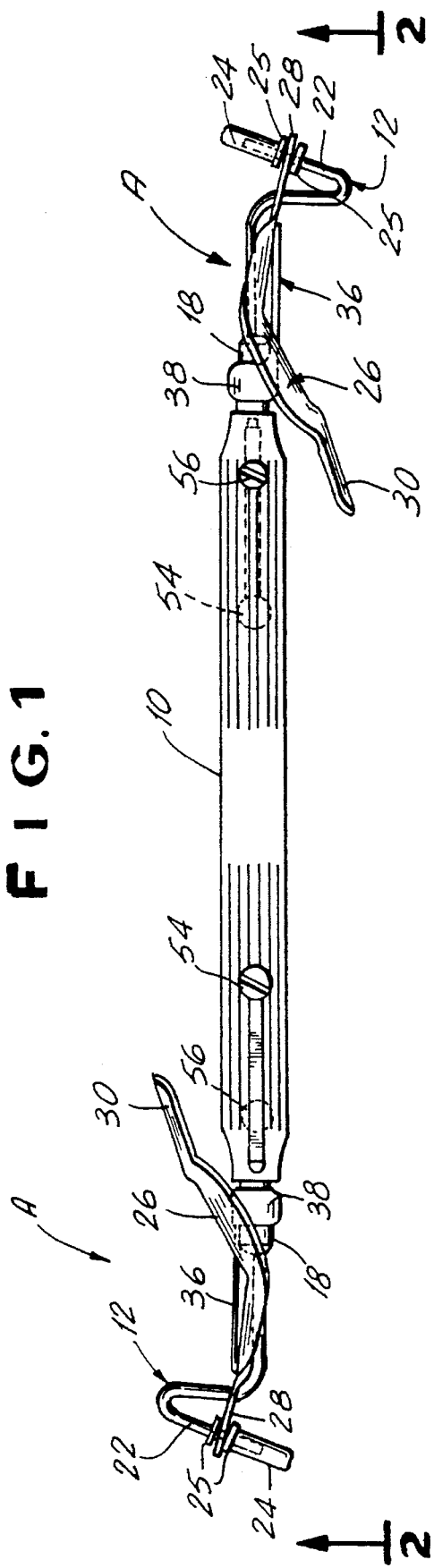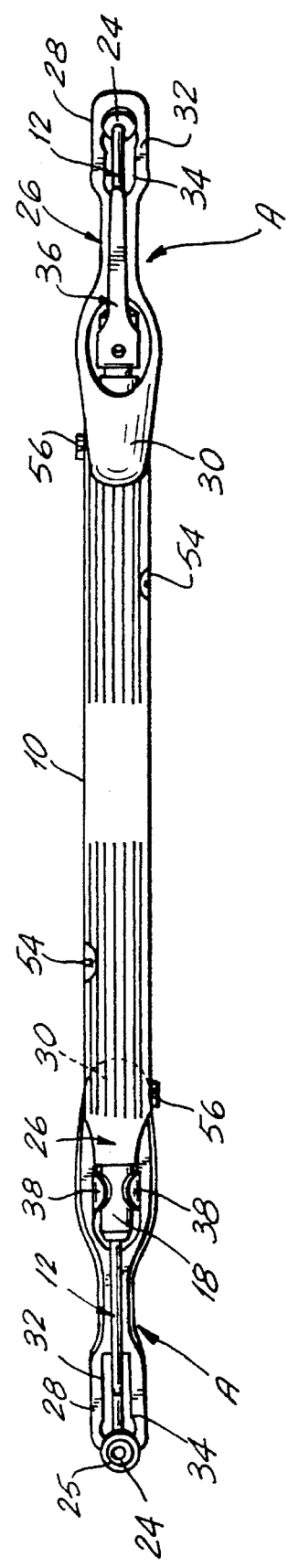

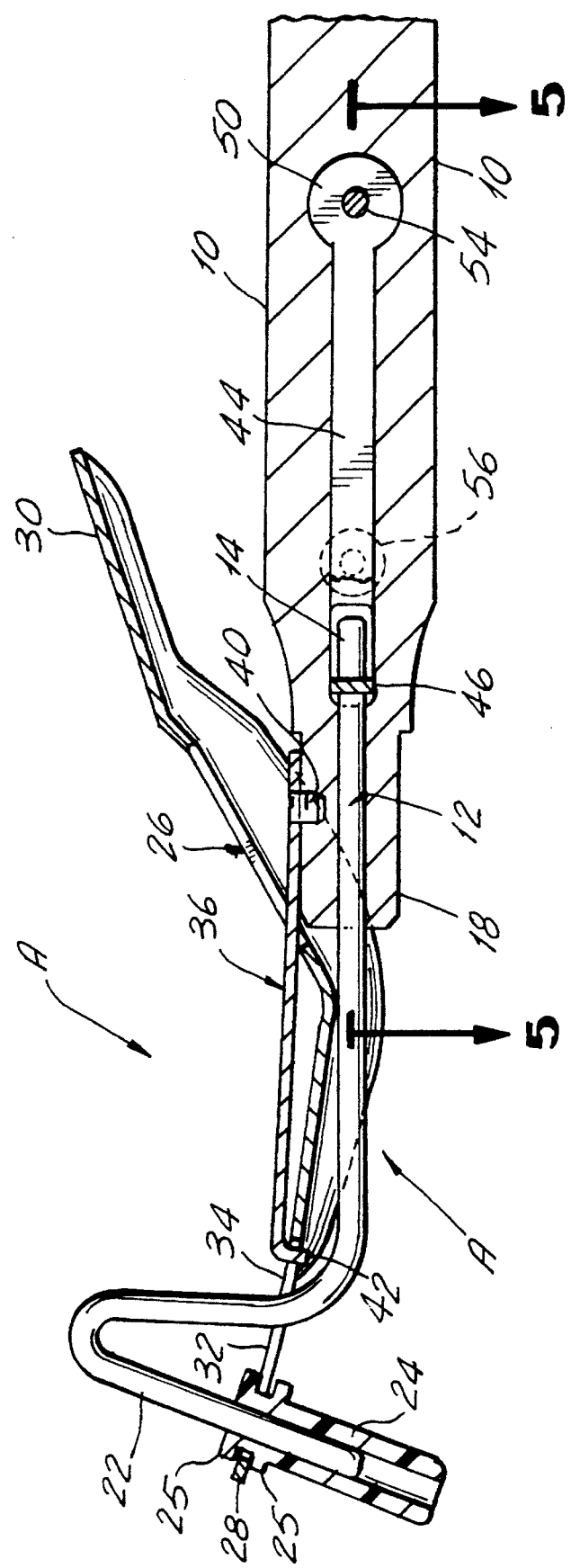

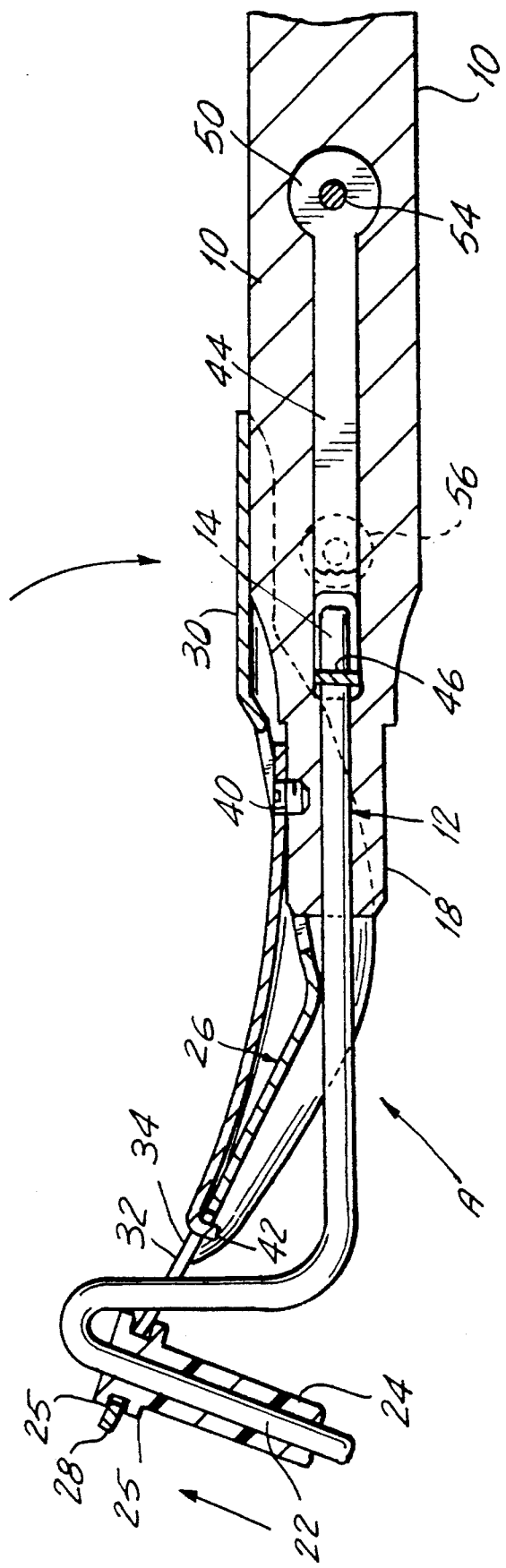

AMALGAM CARRIER

The present invention relates generally to hand held dental instruments, such as amalgam carriers, of the type which include a functional portion and a handle, and more particularly to a mechanism for removably mounting the functional portion of the instrument to the handle such that it can be easily removed as a unit for cleaning purposes.

The need for complete cleaning of dental instruments after each use is well documented, particularly in this era of fatal communicative diseases such as AIDS. However, it is believed that many dentists do not thoroughly clean certain instruments after each use because the parts of the instruments are difficult and time consuming to disassemble, clean and reassemble.

On such instrument is an amalgam carrier. A conventional amalgam carrier consists of a pin, one end of which is received in an opening in the handle. The other end of the pin is bent into a "U" shape. This bent end functions as a plunger which cooperates with an amalgam carrying cylinder mounted on a lever. When the lever is mounted on the pin, it can be moved against the urging of a bias spring relative to the cylinder, to cause the plunger to eject the amalgam. The pin-lever assembly is held on the handle by a tiny set screw which clamps the end of the pin and the bias spring to the handle. Removal of the tiny set screw permits the pin, lever and bias spring to be removed from the handle.

Once the parts are removed from the handle, they will not remain in position relative to each other. Each part must be handled individually so that they can be cleaned and/or sterilized and thereafter reassembled. However, reassembly is difficult and requires substantial dexterity to keep all the parts in proper position while the tiny set screw is inserted into the recess in the handle and rotated. This reassembly process also takes considerable time. Because of this, instruments such as this may not be cleaned as thoroughly and as often as is prudent.

I have overcome this problem by providing a simple mechanism by which the functional assembly of the instrument can be easily and quickly released from the handle as a unit. The set screw remains in place, holding the bias spring on the handle. The parts are easily to clean and/or sterilize in this condition. After cleaning, the lever is positioned on the pin and the assembly is easily reattached to the handle. It snaps into a locked position on the handle in a single motion.

It is, therefore, a prime object of the present invention to provide an improved amalgam carrier in which the functional portion can be quickly and easily removed from the handle for cleaning.

It is another object of the present invention to provide an improved amalgam carrier in which the functional portion includes few parts which can be assembled quickly and easily reattached to the handle after cleaning.

It is another object of the present invention to provide an improved amalgam carrier which includes a minimum of simple parts which can be easily and quickly assembled.

In accordance with the one aspect of the present invention, a dental instrument is provided comprising a handle with an opening and an assembly comprising first means, having an end received within the opening, and second means which are mounted on and moveable relative to the first means. Means are provided for releaseably retaining the assembly on said handle. The retaining means is moveable between a position, wherein the first means end is engaged and the assembly is retained on the handle, and a position, wherein the first means end is disengaged, and the assembly may be removed from the handle. Means accessible from the exterior of the handle are provided for moving the retaining means from the engage position to the disengage position.

Spring means extending from the handle and engaging the second means are provided to bias the second means relative to the first means. The first means comprises a pin which has first and second ends. The first pin end is received within the handle opening and is engaged by the retaining means.

A cylinder is provided on the second means. The second pin end cooperates with the cylinder and functions as a plunger. The second means also includes a first part normally situated adjacent the first means and a second part which extends from the first part forming an obtuse angle therewith. The second means has an opening through which the engaging means extends and is adapted to be engaged by the engaging means.

The retaining means includes a flexible element normally biased toward the engage position. The accessible means includes a pushbutton which when depressed flexes the element against the bias to the disengage the pin end. The element includes a protrusion and the pin end includes a protrusion receiving recess.

In accordance with a second aspect of the invention, an amalgam carrier is provided including a handle with an opening and an assembly comprising a pin and a lever. The pin has with a first end adapted to be received in the opening and a second end. The lever is mounted on and moveable relative to the pin. A cylinder is situated on the lever, with the second pin end received therein. Means are provided for releaseably retaining the assembly on the handle. The retaining means is moveable between a position wherein the first pin end is engaged to retain the assembly on the handle and a position wherein it is disengaged to permit removal of the assembly. Pushbutton means, accessible from the exterior of the handle, are provided for causing the retaining means to move from the engage to the disengage position.

To these and to such other objects which may hereinafter appear, the present invention relates to an improved amalgam carrier as described in detail in the following specification, recited in the annexed claims and illustrated in the accompanying drawings, in which like numerals relate to like parts and in which:

FIG. 1 is a side view of the improved amalgam carrier of the present invention;

FIG. 2 is a view of the carrier of FIG. 1, taken along line 2—2 of FIG. 1;

FIG. 3 is an enlarged cross-sectional view of the pin-lever assembly of the carrier of FIG. 1, with the plunger shown in the rest position;

FIG. 4 is a view similar to FIG. 3, but showing the plunger in the eject position;

As shown in the figures, the improved amalgam carrier of the present invention comprises an elongated metal handle 10 with a functional amalgam carrier assembly, generally designated A, at each end. Each assembly A is identical in structure and function and hence only one will be described.

Figure 6:
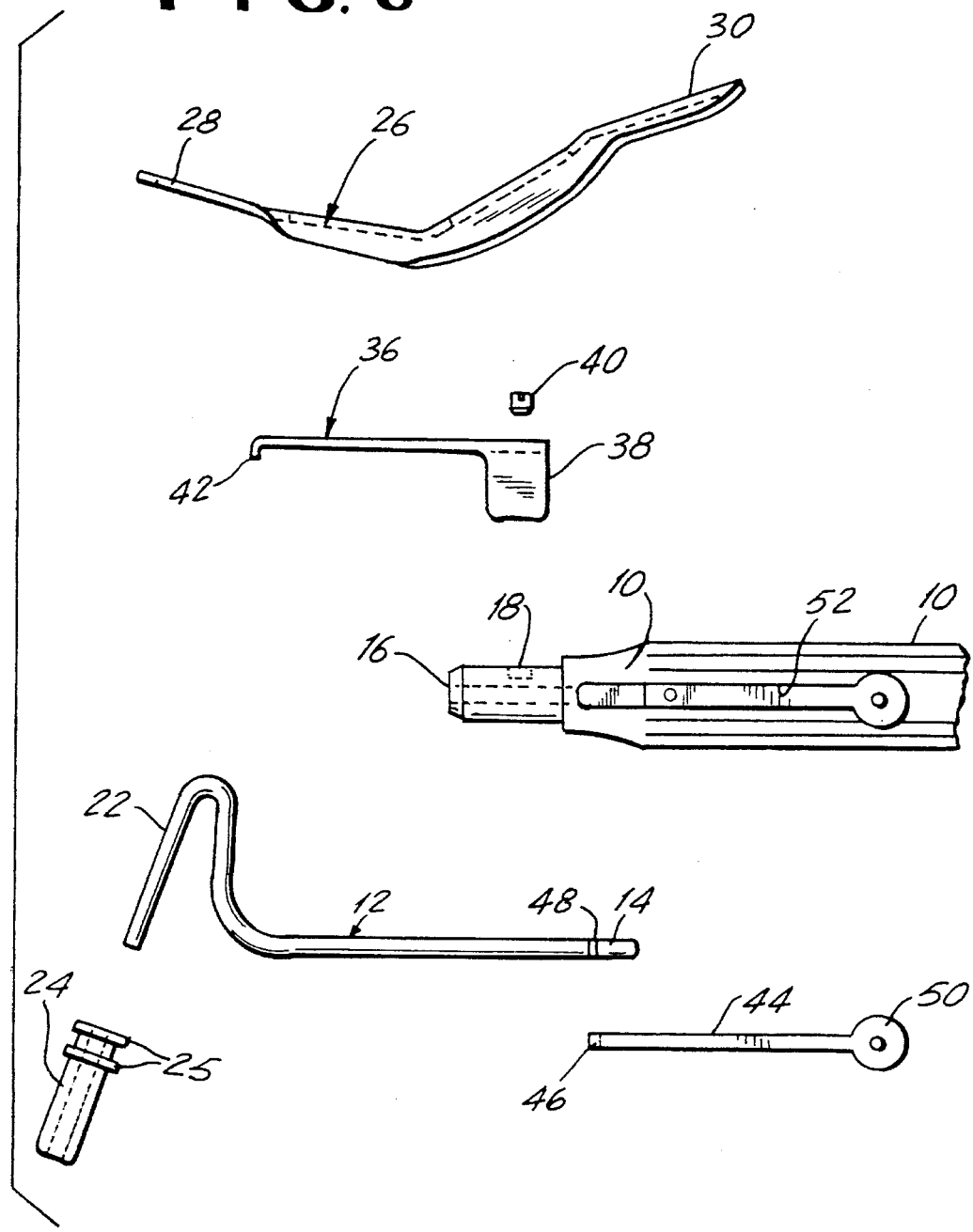
FIG. 6 is an exploded view of the various parts of the carrier.

The individual parts of the assembly A are separately illustrated in FIG. 6. The assembly consists of two main parts. The first part is a pin 12. Pin 12 has a first end 14 adapted to be received in an opening 16 defined by a neck 18 which forms the end of handle 10.

The second end 22 of pin 12 is bent into an inverted "U" shape and is adapted to be received within an open ended cylinder 24. End 22 of pin 12 and cylinder 24 cooperate to form an amalgam retaining cup. End 22 of pin 12 functions as a plunger which is moveable along the interior of cylinder 24. When moved relative to each other, the plunger will cause the amalgam to be ejected from the cup.

Cylinder 24 is provided with a pair of spaced flanges 25 which define a circumferential recess therebetween. Cylinder 24 is mounted on the second main part of the assembly, which is lever 26. Lever 26 has a cylinder carrying end 28 and an actuation end 30. Ends 28 and 30 form an obtuse angle with each other. End 28 has an opening 32 which is defined by a rim 34, as is best seen in FIG. 2. Opening 32 has a cylinder carrying end which is sized so that rim 34 can be received between the flanges 25 to retain the cylinder. The other end of opening 34 is larger than the outer diameter of flanges 25 so as to permit cylinder 24 to be removed from the opening. The inverted "U" end 22 of pin 12 extends through opening 34.

An elongated spring 36 is provided including a body extending from a collar 38. Spring 36 biases lever 26 and, at the same time, engages the lever to retain it in position on pin 12 in a moveable fashion. Collar 38 is commonly affixed to handle neck 18 by a tiny set screw 40 but may be permanently affixed to the handle. The body of spring 36 has a protrusion 42 at its forward end. Protrusion 42 engages rim 34 which defines opening 32 of lever 26.

A flexible element 44 forms a portion of the assembly release means. It is provided at one end with a protrusion 46 for releasably engaging a recess 48 in end 14 of pin 12. The other end of element 44 includes a circular base 50.

Figure 5:
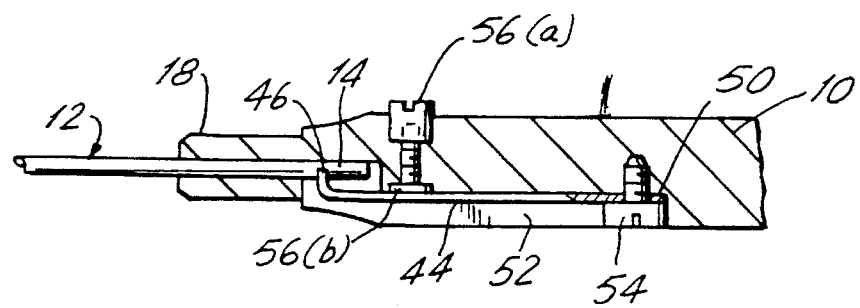
FIG. 5 is an enlarged cross-sectional view of the assembly release mechanism.

Handle 10 is provided with a recess 52 shaped to receive element 44 and its base 50. As best seen in FIG. 5, element 44 is held in recess 52 by a screw 54 which passes through the opening in base 50. In its engaging position, as seen in FIG. 5, protrusion 46 is situated within recess 48 in pin 12 to lock the pin-lever assembly A on handle 10.

FIGS. 3 and 4 illustrate the operation of assembly A. In FIG. 3, the assembly is in the rest position, the end 22 of pin 12 is withdrawn from the end of cylinder 24 so as to form a cup to retain amalgam. The cylinder carrying end 28 of lever 26 is maintained by spring 36 in a position almost parallel to the unbent portion of pin 12. Actuation end 30 of lever 26, forming an obtuse angle with end 28, extends above handle 10 and is accessible to the thumb of the dentist.

As shown in FIG. 4, as the actuation end 30 of lever 26 is depressed, lever 26 pivots against the action of spring 36 and cylinder 24 is moved relative to end 22 of pin 12. As this occurs, the amalgam is ejected from the cylinder.

A pushbutton 56, best seen in FIG. 5, is provided including an accessible portion 56a and an internal shaft portion of 56b, which screw together. Depression of button 56 causes element 44 to move away from pin 14. This removes protrusion 42 from recess 48 and disengages pin 12. Once the pin is disengaged, the pin-lever assembly can be removed from handle 10 by manually moving element 44 away from lever 26, so as to disengage protrusion 42 from rim 34 of lever 26. Spring 36 will remain in place on neck 18 as assembly A is removed unless set screw 40 is removed. Element 44 will remain in place on handle 10, unless screw 54 is removed.

In conventional amalgam carriers, the end of the pin is held within neck by a set screw, similar to screw 40 but of extended length. Accordingly, to remove the assembly, the set screw itself must be removed. When this occurs, spring 36 which biases the lever will become unattached, as well. The individual parts become like a puzzle and must be painstakingly assembled and held in proper relative position as the set screw is replaced to reattach the assembly. This is difficult and time consuming, particularly because the set screw is extremely small, typically having a head which is less than one eight inch in diameter.

The assembly of the present invention is reattached to the handle, as a unit, by placing the lever with the cylinder on the pin and inserting pin end 14 into neck 18. The forward portion of pin end 14 is formed so as to cam protrusion 46 of element 44 out of the way until the protrusion aligns with and engages recess 48. As insertion of the pin is occuring, protrusion 42 of spring 36 moves along the surface of lever 26 until it aligns with rim 34 of opening 32. Once this position is achieved, the assembly locks in place and the instrument is ready for use.

As will now be appreciated, the present invention relates to a dental instrument such as an amalgam carrier in which the functional assembly can be easily and quickly removed from the handle as a unit for thorough cleaning and/or sterilization. The parts can thereafter be reassembled and reattached to the handle as a unit just as easily and quickly. The depression of an externally assessible pushbutton releases an internal locking mechanism which permits the pin of the assembly to be disengaged without the necessity of removing the tiny set screw or bias spring.

While only a single preferred embodiment of the present invention has been disclosed for purposes of illustration, many variations and modifications could be made thereto. It is intended to cover all of these variations and modifications which fall within the scope of the invention, as defined by the following claims:

I claim:

1. A dental instrument comprising a handle with an opening, and an assembly comprising first means having an end received within said opening, second means mounted on and moveable relative to said first means, means for retaining said assembly on said handle, said retaining means being moveable between a position wherein said first means is engaged to retain said assembly on said handle and a position wherein said first means is disengaged to permit removal of said assembly from said handle as a unit and means accessible from the exterior of said handle for moving said retaining means from said engaged position to said disengaged position.

2. The instrument of claim 1 further comprising means extending from said handle for engaging said second means to bias said second means relative to said first means.

3. The instrument of claim 1 wherein said first means comprises a pin having first and second ends and wherein said first pin end is received within said opening and engaged by said retaining means.

4. The instrument of claim 3 further comprising a cylinder and wherein said second pin end cooperates with said cylinder and functions as a plunger.

5. The instrument of claim 4 wherein said cylinder is carried by said second means.

6. The instrument of claim 1 wherein said second means comprises a first part normally situated adjacent said first means and a second part which extends from said first part forming an obtuse angle therewith.

7. The instrument of claim 2 wherein said second means has an opening through which said engaging means extends.

8. The instrument of claim 1 wherein said retaining means comprises flexible means normally biased toward a position to engage said first means and wherein said accessible means comprises depressible means for moving said flexible means to a position wherein said first means is disengaged.

9. The instrument of claim 8 wherein said flexible means comprises a protrusion and said first means comprises a protrusion receiving recess.

10. An amalgam carrier comprising a handle with an opening and an assembly comprising a pin with a first end received in said opening and a second end, a cylinder, a lever mounted on and moveable relative to said pin, said cylinder being situated on said lever with said second pin end therein and means for retaining said assembly on said handle, said retaining means being moveable between a position wherein said first pin end is engaged to retain said assembly on said handle and a position wherein said first pin end is disengaged to permit removal of said assembly as a unit and pushbutton means accessible from the exterior of said handle for moving said retaining means from said engaged position to said disengaged position.

11. The carrier of claim 10 further comprising spring means extending from said handle for biasing said lever relative to said pin.

12. The carrier of claim 11 wherein said lever comprises a first part normally situated adjacent said pin and a second part which extends from said first part forming an obtuse angle therewith.

13. The carrier of claim 11 wherein said lever has an opening through which said spring means extends.

14. The carrier of claim 10 wherein said retaining means comprises a flexible element normally biased toward a position to engage said pin and wherein depression of said push button moves said element to a position wherein said pin is disengaged.

15. The carrier of claim 14 wherein said element comprises a protrusion and said pin comprises a protrusion receiving recess.

* * * * *